United States Patent
Ross et al.

(10) Patent No.: US 9,943,326 B2
(45) Date of Patent: Apr. 17, 2018

(54) ULTRASONIC SURGICAL INSTRUMENTS AND METHODS OF COMPENSATING FOR TRANSDUCER AGING

(71) Applicant: COVIDIEN LP, Mansfield, MA (US)

(72) Inventors: Anthony B. Ross, Boulder, CO (US); David J. Van Tol, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 306 days.

(21) Appl. No.: 14/971,321

(22) Filed: Dec. 16, 2015

(65) Prior Publication Data

US 2016/0206343 A1    Jul. 21, 2016

Related U.S. Application Data

(60) Provisional application No. 62/105,932, filed on Jan. 21, 2015.

(51) Int. Cl.
| | |
|---|---|
| *A61B 17/32* | (2006.01) |
| *A61B 17/00* | (2006.01) |
| *B06B 1/02* | (2006.01) |
| *A61B 90/00* | (2016.01) |

(52) U.S. Cl.
CPC ............. *A61B 17/320092* (2013.01); *A61B 17/00234* (2013.01); *A61B 17/320068* (2013.01);
(Continued)

(58) Field of Classification Search
CPC .......... A61B 17/320068; A61B 2017/320069; A61B 2017/32007; A61B 2017/320071;
(Continued)

(56) References Cited

U.S. PATENT DOCUMENTS

| | | | |
|---|---|---|---|
| 3,839,698 A | 10/1974 | Ehrlich | |
| 4,626,728 A | 12/1986 | Flachenecker et al. | |

(Continued)

FOREIGN PATENT DOCUMENTS

| | | |
|---|---|---|
| DE | 03507672 A1 | 9/1986 |
| DE | 03630478 C1 | 1/1988 |

(Continued)

OTHER PUBLICATIONS

Extended European Search Report corresponding to counterpart Int'l Appln. No. EP 16 15 1211.6, dated May 9, 2016.

*Primary Examiner* — Jonathan Miles

(57) ABSTRACT

An ultrasonic surgical instrument includes a housing, a waveguide extending distally from the housing, an end effector coupled to the distal end of the waveguide, an ultrasonic transducer retained within the housing, and a controller. The ultrasonic transducer is coupled to the proximal end of the waveguide and configured to produce mechanical motion for transmission along the waveguide to the end effector. The controller is configured to control an amplitude of the mechanical motion of the ultrasonic transducer in accordance with at least one amplitude value. The at least one amplitude value is adjusted according to an age of the ultrasonic transducer to compensate for aging of the ultrasonic transducer. Methods for controlling the amplitude of the mechanical motion of an ultrasonic transducer to compensate for aging of the ultrasonic transducer are also provided.

18 Claims, 5 Drawing Sheets

(52) U.S. Cl.
CPC .. *B06B 1/0261* (2013.01); *A61B 2017/00137* (2013.01); *A61B 2017/00185* (2013.01); *A61B 2017/00424* (2013.01); *A61B 2090/0803* (2016.02); *B06B 2201/40* (2013.01)

(58) Field of Classification Search
CPC ....... A61B 2017/320072; A61B 2017/320073; A61B 2017/320074; A61B 2017/320075; A61B 2017/320078; A61B 2017/32008; A61B 2017/320082; A61B 2017/320089; A61B 2017/32009; A61B 17/320092; A61B 2017/320093; A61B 2017/320095; A61B 2017/320094; A61B 2017/320097; A61B 2017/320098; A61B 17/22004; A61B 2017/22005; A61B 2017/22011; A61B 17/22012; A61B 2017/22014; A61B 2017/22015; A61B 2017/22017; A61B 2017/22018; A61B 17/2202; A61B 2017/22021; A61B 17/22022; A61B 2017/22024; A61B 2017/22025; A61B 2017/22027; A61B 2017/22028; A61B 17/22029; A61F 9/00745
See application file for complete search history.

(56) References Cited

U.S. PATENT DOCUMENTS

| | | |
|---|---|---|
| 5,643,353 A | 7/1997 | Wallace et al. |
| 2010/0324580 A1* | 12/2010 | Yamada ......... A61B 17/320092 606/169 |
| 2012/0110758 A1 | 5/2012 | Kanazawa |
| 2015/0073457 A1 | 3/2015 | Stoddard et al. |
| 2015/0073458 A1 | 3/2015 | Stoddard et al. |
| 2015/0201960 A1 | 7/2015 | Akagane |

FOREIGN PATENT DOCUMENTS

| | | |
|---|---|---|
| DE | 20118698 U1 | 4/2003 |
| DE | 20118699 | 4/2003 |
| DE | 20303776 U1 | 7/2004 |
| JP | 61096419 | 5/1986 |
| JP | 63302699 | 12/1988 |
| JP | 02034008 | 2/1990 |
| JP | 06114069 | 4/1994 |
| JP | 2000237204 A | 9/2000 |
| JP | 21212514 | 8/2001 |
| JP | 2001212514 A | 8/2001 |
| JP | 2001346805 A | 12/2001 |
| JP | 2002045368 A | 2/2002 |
| JP | 2002186901 A | 7/2002 |
| JP | 24254128 | 9/2004 |
| JP | 3696034 B2 | 9/2005 |
| JP | 3756726 B2 | 3/2006 |
| JP | 2012096193 A | 5/2012 |
| WO | 2005/122917 A1 | 12/2005 |
| WO | 2007/014183 A2 | 2/2007 |
| WO | 2007014548 A2 | 2/2007 |
| WO | 2014/178436 A1 | 11/2014 |

* cited by examiner

ULTRASONIC SURGICAL INSTRUMENTS AND METHODS OF COMPENSATING FOR TRANSDUCER AGING

CROSS REFERENCE TO RELATED APPLICATION

The present application claims the benefit of and priority to U.S. Provisional Application Ser. No. 62/105,932, filed on Jan. 21, 2015, the entire contents of which are incorporated herein by reference.

BACKGROUND

Technical Field

The present disclosure relates to ultrasonic surgical instruments and, more particularly, to ultrasonic surgical instruments and methods of compensating for transducer aging.

Background of Related Art

Ultrasonic surgical instruments utilize ultrasonic energy, i.e., ultrasonic vibrations, to treat tissue. More specifically, ultrasonic surgical instruments utilize mechanical vibration energy transmitted at ultrasonic frequencies to coagulate, cauterize, fuse, seal, cut, desiccate, fulgurate, or otherwise treat tissue.

Typically, an ultrasonic surgical instrument is configured to transmit ultrasonic energy produced by a generator and transducer assembly along a waveguide to an end effector that is spaced-apart from the generator and transducer assembly. With respect to cordless ultrasonic instruments, for example, a portable power source, e.g., a battery, and the generator and transducer assembly are mounted on the handheld instrument itself, while the waveguide interconnects the generator and transducer assembly and the end effector. Wired ultrasonic instruments operate in similar fashion except that, rather than having the generator and power source mounted on the handheld instrument itself, the handheld instrument is configured to connect to a standalone power supply and/or generator via a wired connection.

Regardless of the particular type and/or configuration of ultrasonic surgical instrument utilized, the various components thereof are typically calibrated during manufacturing and/or assembly to ensure a desired ultrasonic energy is produced at the end effector. Calibration may also be intermittently performed, manually or automatically, before, during, after, and/or between uses.

SUMMARY

As used herein, the term "distal" refers to the portion that is being described which is further from a user, while the term "proximal" refers to the portion that is being described which is closer to a user. Further, to the extent consistent any or all of the aspects detailed herein may be used in conjunction with any or all of the other aspects detailed herein.

In accordance with aspects of the present disclosure, an ultrasonic surgical instrument is provided including a housing, a waveguide, an end effector, an ultrasonic transducer, and a controller. The waveguide includes a proximal end and a distal end and extends distally from the housing. The end effector is coupled to the distal end of the waveguide. The transducer assembly is retained within the housing and includes an ultrasonic transducer and a controller. The ultrasonic transducer is coupled to the proximal end of the waveguide and is configured to produce mechanical motion for transmission along the waveguide to the end effector. The controller is configured to control an amplitude of the mechanical motion of the ultrasonic transducer in accordance with at least one amplitude value. The at least one amplitude value is adjusted according to an age of the ultrasonic transducer to compensate for aging of the ultrasonic transducer.

In aspects of the present disclosure, the at least one amplitude value is adjusted to compensate for aging effects of the ultrasonic transducer in order to maintain constant the amplitude of the mechanical motion. In order to do so, the at least one amplitude value may, for example, be decreased as the ultrasonic transducer ages and/or may be adjusted logarithmically with respect to the age of the ultrasonic transducer.

In aspects of the present disclosure, the at least one amplitude value includes a first amplitude value corresponding to a low power mode and a second amplitude value corresponding to a high power mode.

In aspects of the present disclosure, the controller includes a memory storing information indicating a time t=0 from which an age of the ultrasonic transducer is determined. The time t=0 may correspond to occurrence of a pre-determined event associated with the ultrasonic transducer, e.g., where the ultrasonic transducer includes a piezoelectric stack, time t=0 may correspond to when the piezoelectric stack is secured under compression.

An assembly provided in accordance with aspects of the present disclosure and configured for use with an ultrasonic surgical instrument includes an ultrasonic transducer configured to produce mechanical motion and a controller configured to control an amplitude of the mechanical motion of the ultrasonic transducer in accordance with at least one amplitude value. The controller includes a memory storing information indicating a time t=0 from which an age of the ultrasonic transducer is determined, and is configured to adjust the at least one amplitude value according to the age of the ultrasonic transducer.

In aspects, the at least one amplitude value is adjusted to compensate for aging effects of the ultrasonic transducer in order to maintain constant the amplitude of the mechanical motion.

In aspects, the at least one amplitude value is decreased as the age of the ultrasonic transducer increases. Alternatively or additionally, the at least one amplitude value may be adjusted logarithmically with respect to the age of the ultrasonic transducer.

In aspects, the time t=0 corresponds to occurrence of a pre-determined event associated with the ultrasonic transducer. For example, in aspects where the ultrasonic transducer includes a piezoelectric stack, the time t=0 may correspond to when the piezoelectric stack is secured under compression.

A method of controlling an ultrasonic transducer, e.g., of an ultrasonic surgical instrument, provided in accordance with aspects of the present disclosure includes controlling an amplitude of mechanical motion of an ultrasonic transducer in accordance with at least one amplitude value, determining an age of the ultrasonic transducer, and adjusting the at least one amplitude value in accordance with the age of the ultrasonic transducer.

In aspects, wherein determining the age of the ultrasonic transducer includes using a clock to measure the age of the ultrasonic transducer relative to a time t=0.

In aspects, the time t=0 corresponds to occurrence of a pre-determined event associated with the ultrasonic transducer. For example, where the ultrasonic transducer includes a piezoelectric stack, the time t=0 may correspond to when the piezoelectric stack is secured under compression.

In aspects, the at least one amplitude value is decreased as the age of the ultrasonic transducer increases.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and.

DETAILED DESCRIPTION

Figure 1A:
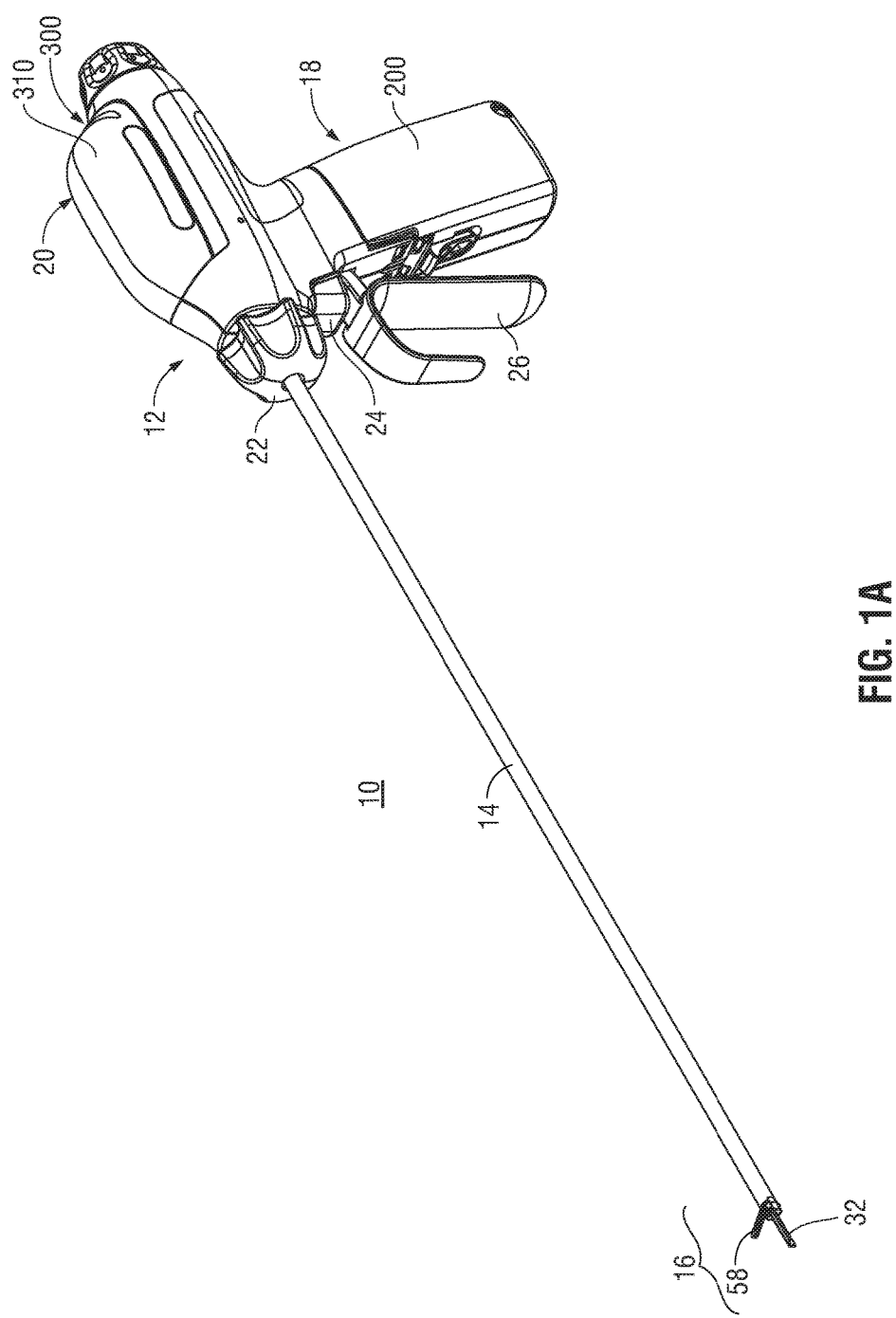
FIG. 1A is a side, perspective view of an ultrasonic surgical instrument provided in accordance with the present disclosure, wherein the tool assembly is disposed in an open condition.

Referring generally to FIGS. 1A-4, an embodiment of an ultrasonic surgical instrument exemplifying the aspects and features of the present disclosure is shown generally identified by reference numeral 10. As detailed below, integrated within ultrasonic surgical instrument 10 are features that enable automatic compensation for transducer aging, thus helping to ensure that ultrasonic surgical instrument 10 enjoys consistent performance throughout its usable life. However, it is also contemplated that the transducer aging compensation features of the present disclosure be incorporated into or used with any other suitable ultrasonic surgical instrument, incorporated into an energy source, e.g., a stand-alone generator (not shown), associated with an ultrasonic surgical instrument, and/or utilized to allow for manual adjustment of the parameters and/or settings associated with the transducer of ultrasonic surgical instrument 10 or other suitable ultrasonic surgical instrument.

For the purposes herein, ultrasonic surgical instrument 10 is generally described. Aspects and features of ultrasonic surgical instrument 10 not germane to the understanding of the transducer aging compensation features provided in accordance with the present disclosure are omitted to avoid obscuring such aspects and features of the present disclosure in unnecessary detail.

With reference to FIGS. 1A-3B, ultrasonic surgical instrument 10 generally includes a handle assembly 12, an elongated body portion 14, and a tool assembly 16. Tool assembly 16 includes a blade 32 and a clamp member 58. Handle assembly 12 supports a battery assembly 18 and an ultrasonic transducer and generator assembly ("TAG") 20, and includes a rotatable nozzle 22, an activation button 24, and a clamp trigger 26. Battery assembly 18 and TAG 20 are each releasably secured to handle assembly 12, and are removable therefrom to facilitate disposal of the entire device, with the exception of battery assembly 18 and TAG 20. However, it is contemplated that any or all of the components of ultrasonic surgical instrument 10 be configured as disposable single-use components or sterilizable multi-use components.

Figure 1B:
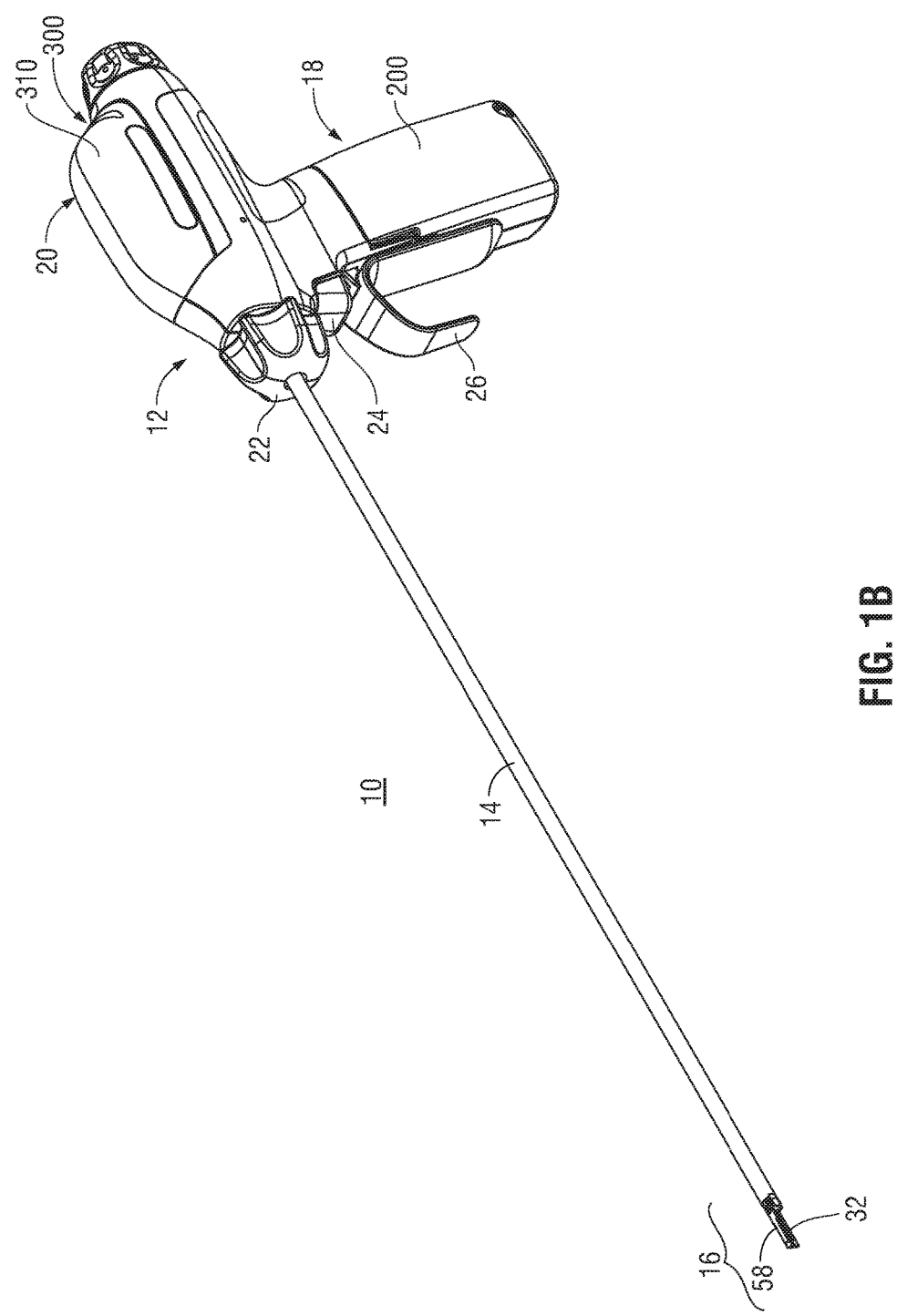
FIG. 1B is a side, perspective view of the ultrasonic surgical instrument of FIG. 1A, wherein the tool assembly is disposed in a clamping condition.
Figure 2:
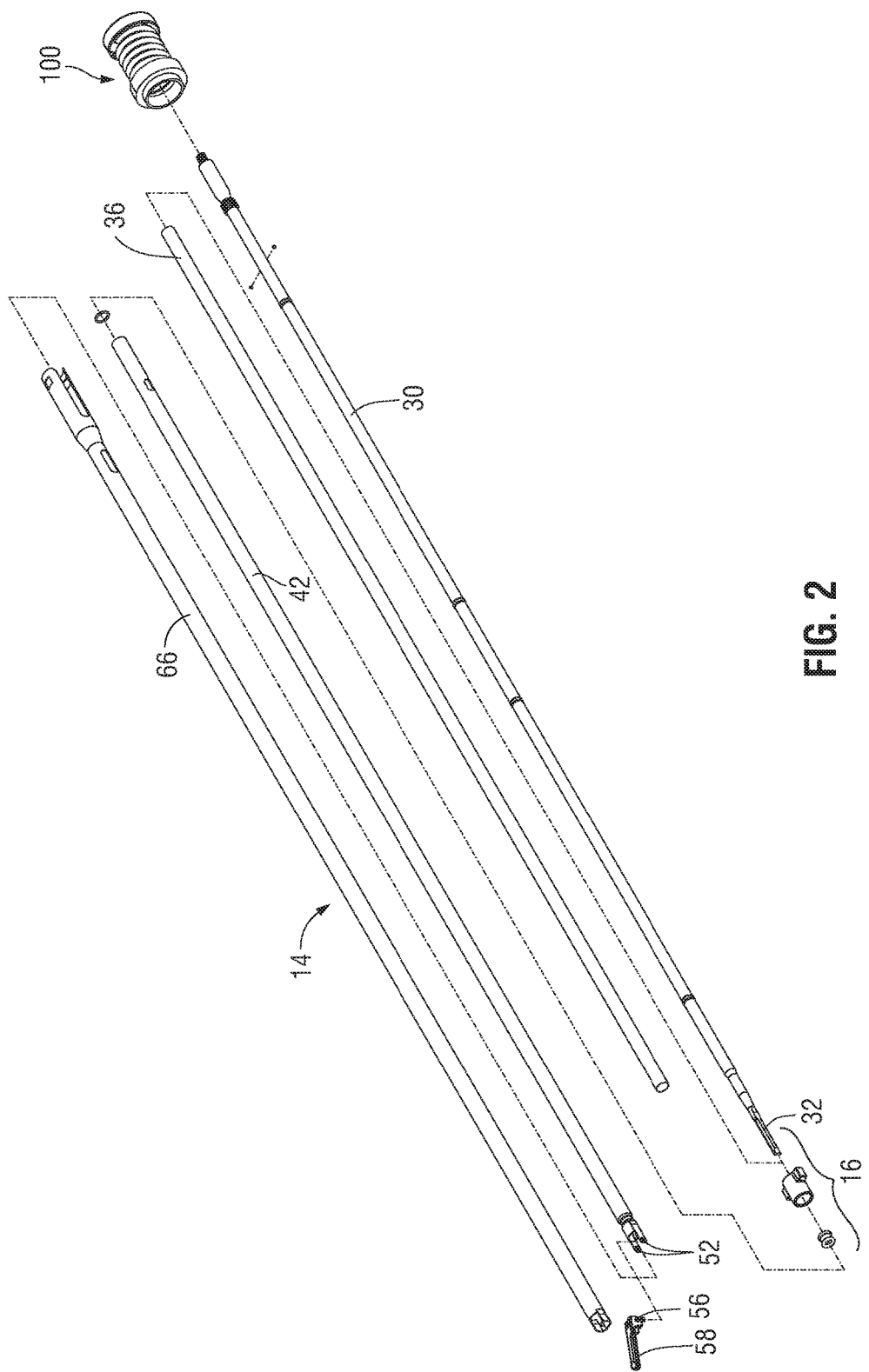
FIG. 2 is an exploded, perspective view of the shaft, waveguide, and tool assemblies of the ultrasonic surgical instrument of FIG. 1A.
Figure 3A:
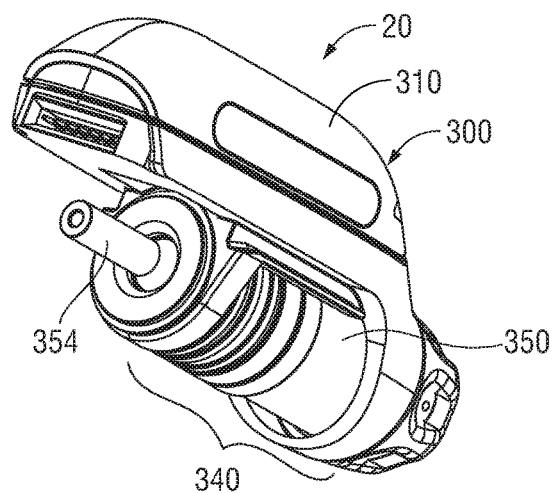
FIG. 3A is a side, perspective view of the ultrasonic transducer and generator assembly ("TAG") of the ultrasonic surgical instrument of FIG. 1A.
Figure 3B:
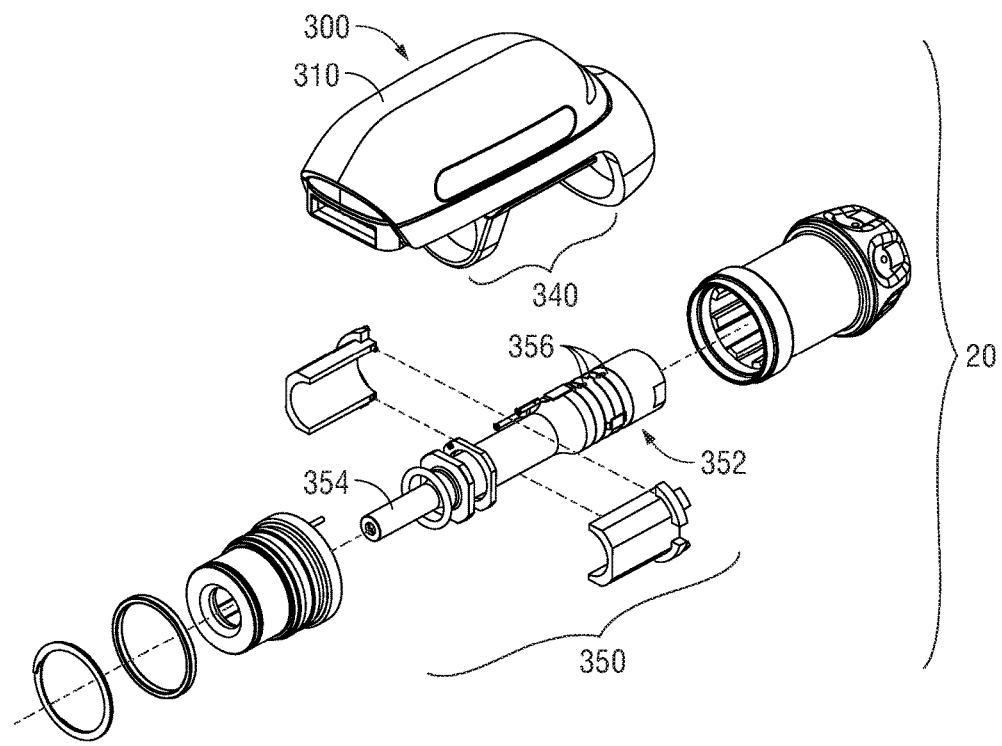
FIG. 3B is an exploded, perspective view of the TAG of the ultrasonic surgical instrument of FIG. 1A.

Referring to FIG. 2 in particular, elongated body portion 14 includes a waveguide 30 which extends distally from handle assembly 12 to tool assembly 16. A distal end of waveguide 30 defines a blade 32. A proximal end of waveguide 30 is configured to engage TAG 20 (FIGS. 3A and 3B), as detailed below. An isolation tube 36 is positioned about waveguide 30 to prevent the transfer of ultrasonic energy from waveguide 30 to an inner support tube 42. Waveguide 30 and inner support tube 42 are rotatably coupled to rotatable nozzle 22 (FIGS. 1A and 1B) such that rotation of nozzle 22 (FIGS. 1A and 1B) effects corresponding rotation of inner support tube 42 and waveguide 30. An actuator tube 66 which, as detailed below, is coupled to inner support tube 42, is similarly rotated upon rotation of nozzle 22 (FIGS. 1A and 1B).

Inner support tube 42 is positioned about isolation tube 36 and includes a distal end having a pair of spaced clamp support arms 52. Spaced clamp support arms 52 are configured to pivotally engage pivot members 56 (only one of which is visible in FIG. 2) formed on clamp member 58 of tool assembly 16 to enable pivoting of clamp member 58 between an open position (FIG. 1A), wherein clamp member 58 is spaced from blade member 32, and a closed position (FIG. 1B), wherein clamp member 58 is approximated relative to blade member 32. Clamp member 58 is moved between the open and closed positions in response to actuation of clamp trigger 26 (FIGS. 1A and 1B).

Outer actuator tube 66 is slidably supported about inner support tube 42 and is operably coupled to clamp member 58 such that, as actuator tube 66 is slid about inner support tube 42 between an advanced position and a retracted position, clamp member 58 is pivoted from the open position (FIG. 1A) to the closed position (FIG. 1B). A proximal end of outer actuator tube 66 is operably coupled with rotatable nozzle 22 such that outer actuator tube 66 is rotatably secured to but slidable relative to rotatable nozzle 22. The proximal end of outer actuator tube 66 is also operably coupled with a drive mechanism 100.

Referring to FIGS. 1A-2, handle assembly 12 includes drive mechanism 100 supported therein for linear movement relative to handle assembly 12. Handle assembly 12 also includes the aforementioned clamp trigger 26, which is operably coupled with drive mechanism 100 such that, in use, when clamping trigger 26 is compressed towards battery assembly 18 (FIG. 1B), outer actuator tube 66 is moved from the advanced position to the retracted position to pivot clamp member 58 from the open position to the closed position in relation to blade 32. A spring (not explicitly shown) may be provided to bias clamping trigger 26 towards the initial position and, thus, clamp member 58 towards the open position (FIG. 1A).

Figure 4:
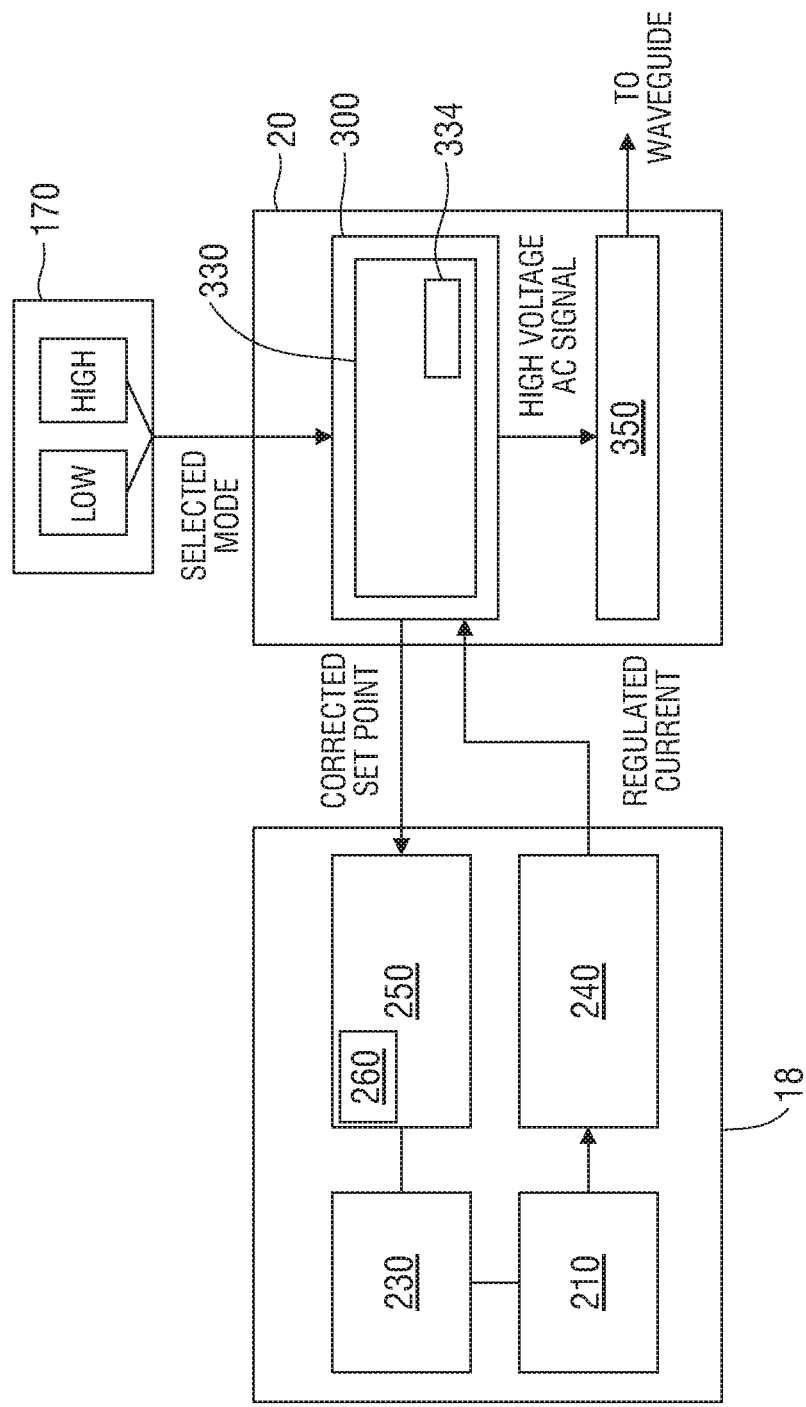
FIG. 4 is a block diagram illustrating the power and signal communications between the TAG, battery assembly, and switch assembly of the ultrasonic surgical instrument of FIG. 1A.

With additional reference to FIG. 4, activation button 24 is supported on handle assembly 12. When activation button 24 is activated in an appropriate manner, an underlying two-mode switch assembly 170 is activated to effect communication between battery assembly 18 and TAG 20 in either a "LOW" power mode or a "HIGH" power mode, depending upon the manner of activation of activation button 24.

Battery assembly 18 is connected to a lower end of handle assembly 12 to define a fixed handgrip portion of handle assembly 12 and includes an outer housing 200 that houses one or more battery cells 210, a safety circuit and fuel gauge board 230, a buck converter 240, and a battery microcontroller 250 including a clock 260. Safety circuit and fuel gauge board 230 of battery assembly 18 controls the charging and discharging of battery cells 210, monitors parameters of battery cells 210, and protects battery cells 210. Buck converter 240 and battery microcontroller 250 are detailed below. Clock 260 may be configured as a real-time clock from which, in conjunction with the birthdate of ultrasonic transducer 350, e.g., time t=0, the age of ultrasonic transducer 350 can be determined. A series of contacts (not explicitly shown) enable communication of power and/or control signals between the internal components of battery assembly 18, two-mode switch assembly 170, and TAG 20, although contactless communication therebetween is also contemplated.

Referring to FIGS. 1A, 1B, and 3A-4, TAG 20 includes a generator 300 and an ultrasonic transducer 350. Generator 300 includes an outer housing 310 that houses a TAG microcontroller 330 having a memory 334. Memory 334 stores set point data corresponding to the "LOW" and "HIGH" power modes of ultrasonic surgical instrument 10 as well as the "birthdate" of ultrasonic transducer 350 and aging compensation data in the form of one or more values, functions, tables, and/or multipliers. This data, in accordance with the age of ultrasonic transducer 350, as determined using clock 260 of battery assembly 18 and the "birthdate" of ultrasonic transducer 350 stored in memory 334 of TAG microcontroller 330, are utilized to compensate for effects of aging of ultrasonic transducer 350 and correct the set point values accordingly, as detailed below.

TAG 20 includes support members 340 extending from outer housing 310 that define cradles for rotatably supporting ultrasonic transducer 350. Ultrasonic transducer 350 includes a piezoelectric stack 352 and a forwardly extending horn 354. Horn 354 is configured to threadably engage the proximal end of waveguide 30 (FIG. 2), although other suitable engagement mechanisms are also contemplated. A series of contacts (not explicitly shown) associated with TAG 20 enable communication of power and/or control signals between TAG 20, battery assembly 18, and two-mode switch assembly 170, although contactless communication therebetween is also contemplated.

In general, in use, when battery assembly 18 and TAG 20 are attached to handle assembly 12 and waveguide 30 and ultrasonic surgical instrument 10 is activated, battery cells 210 provide power to generator 300 of TAG 20 which, in turn, uses this power to apply an AC signal to ultrasonic transducer 350 of TAG 20. Ultrasonic transducer 350, in turn, converts the AC signal into high frequency mechanical motion. This high frequency mechanical motion produced by ultrasonic transducer 350 is transmitted to blade 32 via waveguide 30 for application of such ultrasonic energy tissue adjacent to or clamped between blade 32 and clamp member 58 of tool assembly 16 to treat tissue.

More specifically, in use, when activation button 24 is manipulated such that switch assembly 170 is activated in the "LOW" power mode, switch assembly 170 signals TAG microcontroller 330 to provide microcontroller 250 of battery assembly 18 with an amplitude value corresponding to the "LOW" power mode amplitude set point. Microcontroller 250 of battery assembly 18 regulates the current output from buck converter 240 to TAG 20 in accordance with this "LOW" power mode amplitude value such that an appropriate current is applied to TAG 20 to enable generator 300 to generate a high voltage AC signal that is applied to ultrasonic transducer 350 for producing a mechanical motion having an amplitude equal to a "LOW" power mode amplitude set point. Similarly, when activation button 24 is manipulated such that switch assembly 170 is activated in the "HIGH" power mode, switch assembly 170 signals TAG microcontroller 330 to provide microcontroller 250 of battery assembly 18 with an amplitude value corresponding to the "HIGH" power mode amplitude set point. Microcontroller 250 of battery assembly 18 regulates the current output from buck converter 240 to TAG 20 in accordance with this "HIGH" power mode amplitude value such that an appropriate current is applied to TAG 20 to enable generator 300 to generate a high voltage AC signal that is applied to ultrasonic transducer 350 for producing a mechanical motion having an amplitude equal to a "HIGH" power mode amplitude set point.

Ultrasonic transducer 350, as noted above, includes a piezoelectric stack 352. It is piezoelectric stack 352 of ultrasonic transducer 350 that converts the high voltage AC signal into mechanical motion that is transmitted from ultrasonic transducer 350, along waveguide 30, to blade 32 for treating tissue. Piezoelectric stack 352 includes a plurality of piezoelectric elements 356 stacked and bolted to one another under compression such that, in use, upon application of the high voltage AC signal to piezoelectric stack 352, the piezoelectric elements 356 repeatedly deform and reform, thus producing the mechanical motion of ultrasonic transducer 350 that is output to waveguide 30 for transmission therealong to blade 32.

It has been found that, with respect to transducers including piezoelectric materials, aging of the transducer affects the amplitude of mechanical motion output from the transducer. Thus, with respect to ultrasonic transducer 350, for example, if the "LOW" and "HIGH" power mode amplitude values provided to microcontroller 250 of battery assembly 18 are fixed at their respective set points throughout the usable life of ultrasonic transducer 350, the amplitude of the resulting mechanical motion produced by ultrasonic transducer 350 may drift from these set points as ultrasonic transducer 350 ages. In other words, the actual output may no longer be equal to the set point. Thus, correction is required to compensate for transducer aging.

Additionally, such aging, or at least a particular pattern of aging, has been determined to be a result of, and can be measured from, occurrence of an "event" associated with the ultrasonic transducer such as polarization, compression, or heating. With respect to ultrasonic transducer 350 in particular, it has been found that bolting of piezoelectric elements 356 under compression to form piezoelectric stack 352 is one such "event" and, accordingly, that the age of ultrasonic transducer 350 may be determined by setting the time at which piezoelectric elements 356 are bolted under compression, e.g., the "birthdate" of ultrasonic transducer 350, to time t=0. Time t=0 may be set by writing this "birthdate" time into memory 334 of TAG microcontroller 330, or in any other suitable fashion. The actual age of ultrasonic transducer 350 at any given point may be determined by comparing the "birthdate" time stored in memory 334 with the time provided by clock 260 of battery assembly 18. Further, it is contemplated that other "events" such as polarization, heating, or another point during manufacturing, assembly, and/or use may also be utilized to mark time t=0.

The aging characteristics of a transducer from a given "'event" or time t=0 may be measured experimentally, estimated, or otherwise determined. Further, such aging effects may be represented by a value or values, e.g., a value(s) that is to be added to or subtracted from an original set point, and/or by an equation or equations, e.g., an equation(s) into which the original set point is input, that are used to correct the set points to compensate for transducer aging. With respect to transducer 350, for example, experimental data has indicated that the output amplitude of transducer 350 corresponding to an original set point "$S_0$" increases as a function of time. Thus, in order to compensate for transducer aging and produce an output amplitude that is equal to the original set point "$S_0$" for a given time, aging compensation is performed by subtracting a correction value "C" or correction function "C(t)" from the original set point "$S_0$" to obtain an age-compensated, or corrected set point value "$S_t$" according to equations (1), wherein the correction is in the form of a value, or (2), wherein the correction is in the form of a function:

$$S_t = S_0 - C \quad (1)$$

$$S_t = S_0 - C(t) \quad (2)$$

More specifically, such experimental data has found that, for a "LOW" power mode original set point $S_{0(LOW)}$=0.00238 in, the output amplitude increases logarithmically for time 10≤t≤100, wherein "t" is represented in days, in a manner such that aging compensation can be accomplished using equation (2), above, wherein the correction function "$C_{LOW}(t)$" is provided according to equation (3):

$$C_{LOW}(t) = 0.12 * \text{Log}_{10}(t/10) * 0.001 \text{ in} \quad (3)$$

It has further been found that, for a "HIGH" power mode original set point $S_{0(HIGH)}$=0.00315 in, the output amplitude increases logarithmically for time 10≤t≤100, wherein "t" is represented in days, in a manner such that aging compensation can be accomplished using equation (2), above, wherein the correction function "$C_{HIGH}(t)$" is provided according to equation (4):

$$C_{HIGH}(t) = 0.15 * \text{Log}_{10}(t/10) * 0.001 \text{ in} \quad (4)$$

For time t>100 and the "LOW" power mode original set point $S_{0(LOW)}$=0.00238 in, an average offset value has been observed such that aging compensation can be accomplished using equation (1), above, wherein the correction value "$C_{LOW}$" is provided by equation (5):

$$C_{LOW} = 0.12 * 0.001 \text{ in} \quad (5)$$

For time t>100 and the "HIGH" power mode original set point $S_{0(HIGH)}$=3.15 mm, an average offset value has been observed such that aging compensation can be accomplished using equation (1), above, wherein the correction value "$C_{HIGH}$" is provided by equation (6):

$$C_{HIGH} = 0.15 * 0.001 \text{ in} \quad (6)$$

The above-noted equations and experimental data are provided for exemplary purposes only, as transducer aging for any given surgical instrument may vary depending upon the specifications and/or configuration of the particular transducer and/or other components of the surgical instrument. Further, experimental data need not be used but, rather, transducer aging information may be provided via estimations, simulations, projections, models, etc.

As detailed below, based upon the transducer aging information and the correction offset values and/or functions, the original set point "$S_0$" can be corrected to obtain a corrected set point value "$S_t$" such that the actual output amplitude of displacement of ultrasonic transducer 350 can be maintained at the original set point "$S_0$" despite aging of ultrasonic transducer 350.

The above-detailed information is stored in memory 334 of TAG microcontroller 330 for use in determining the corrected set point value "$S_t$" provided from TAG microcontroller 330 to microcontroller 250 of battery assembly 18. More specifically, such information may be stored: as a function or functions from which, in conjunction with the age of ultrasonic transducer 350 as determined using clock 260, the corrected set point value "$S_t$" may be calculated; as a look-up table that correlates the corrected set point value "$S_t$" with the age of ultrasonic transducer 350 as determined using clock 260; or in any other suitable fashion. As noted in the example above, a different function or value may be provided for a different time range, and/or for a different setting, e.g., the "LOW" power mode versus the "HIGH" power mode.

In use, TAG microcontroller 350 accesses and/or determines the corrected set point value "$S_t$" corresponding to the age of ultrasonic transducer 350 and provides the corrected set point value "$S_t$" to microcontroller 250 of battery assembly 18. Such adjustment may be performed continuously, e.g., each time ultrasonic surgical instrument 10 is activated, at periodic intervals, e.g., every 10 days, and/or manually, e.g., upon request. Further, it is contemplated that TAG microcontroller 330 be externally accessible, e.g., wirelessly or via a wired connection, to enable updating and/or modification of the "birthdate" and/or age compensation information stored in memory 334.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasonic surgical instrument, comprising:
   a housing;
   a waveguide having a proximal end and a distal end, the waveguide extending distally from the housing;
   an end effector coupled to the distal end of the waveguide;
   an ultrasonic transducer retained within the housing and coupled to the proximal end of the waveguide, the ultrasonic transducer configured to produce mechanical motion for transmission along the waveguide to the end effector; and
   a controller configured to control an amplitude of the mechanical motion of the ultrasonic transducer in accordance with at least one amplitude value, wherein the at least one amplitude value is adjusted according to an age of the ultrasonic transducer.

2. The ultrasonic surgical instrument according to claim 1, wherein the at least one amplitude value is adjusted to compensate for aging effects of the ultrasonic transducer in order to maintain constant the amplitude of the mechanical motion.

3. The ultrasonic surgical instrument according to claim 1, wherein the at least one amplitude value is decreased as the ultrasonic transducer ages.

4. The ultrasonic surgical instrument according to claim 1, wherein the at least one amplitude value is adjusted logarithmically with respect to an age of the ultrasonic transducer.

5. The ultrasonic surgical instrument according to claim 1, wherein the at least one amplitude value includes a first amplitude value corresponding to a low power mode and a second amplitude value corresponding to a high power mode.

6. The ultrasonic surgical instrument according to claim 1, wherein the controller includes a memory storing information indicating a time t=0 from which an age of the ultrasonic transducer is determined, and wherein the time t=0 corresponds to occurrence of a pre-determined event associated with the ultrasonic transducer.

7. The ultrasonic surgical instrument according to claim 6, wherein the ultrasonic transducer includes a piezoelectric stack, and wherein the time t=0 corresponds to when the piezoelectric stack is secured under compression.

8. An assembly for use with an ultrasonic surgical instrument, the assembly including:
   an ultrasonic transducer configured to produce mechanical motion; and
   a controller configured to control an amplitude of the mechanical motion of the ultrasonic transducer in accordance with at least one amplitude value, the controller including a memory storing information indicating a time t=0 from which an age of the ultrasonic transducer is determined, wherein the at least one amplitude value is adjusted according to the age of the ultrasonic transducer.

9. The assembly according to claim 8, wherein the at least one amplitude value is adjusted to compensate for aging effects of the ultrasonic transducer in order to maintain constant the amplitude of the mechanical motion.

10. The assembly according to claim 8, wherein the at least one amplitude value is decreased as the age of the ultrasonic transducer increases.

11. The assembly according to claim 8, wherein the at least one amplitude value is adjusted logarithmically with respect to the age of the ultrasonic transducer.

12. The assembly according to claim 8, wherein the time t=0 corresponds to occurrence of a pre-determined event associated with the ultrasonic transducer.

13. The assembly according to claim 12, wherein the ultrasonic transducer includes a piezoelectric stack, and wherein the time t=0 corresponds to when the piezoelectric stack is secured under compression.

14. A method of controlling an ultrasonic transducer for a surgical instrument, comprising:
   controlling an amplitude of mechanical motion of an ultrasonic transducer in accordance with at least one amplitude value;
   determining an age of the ultrasonic transducer; and
   adjusting the at least one amplitude value in accordance with the age of the ultrasonic transducer.

15. The method according to claim 14, wherein determining the age of the ultrasonic transducer includes using a clock to measure the age of the ultrasonic transducer relative to a time t=0.

16. The method according to claim 15, wherein the time t=0 corresponds to occurrence of a pre-determined event associated with the ultrasonic transducer.

17. The method according to claim 16, wherein the ultrasonic transducer includes a piezoelectric stack, and wherein the time t=0 corresponds to when the piezoelectric stack is secured under compression.

18. The method according to claim 14, wherein the at least one amplitude value is decreased as the age of the ultrasonic transducer increases.

* * * * *